United States Patent [19]

Juncos et al.

[11] Patent Number: 4,615,183
[45] Date of Patent: Oct. 7, 1986

[54] COLD PLATE FOR LABORATORY USE

[75] Inventors: Jorge L. Juncos, Silver Springs, Md.; Edward Wellner, Fairfax, Va.; Paul Smith, Annapolis, Md.

[73] Assignee: The United States of America as represented by the Department of Health and Human Services, Washington, D.C.

[21] Appl. No.: 748,207

[22] Filed: Jun. 24, 1985

[51] Int. Cl.⁴ ............................................. B01F 3/04
[52] U.S. Cl. ...................................... 62/306; 62/458
[58] Field of Search ................. 62/78, 306, 458, 440

[56] References Cited

U.S. PATENT DOCUMENTS

| | | |
|---|---|---|
| 1,052,707 | 2/1913 | Allen . |
| 1,552,949 | 9/1925 | Platten . |
| 1,852,707 | 4/1932 | Hoffman . |
| 2,058,871 | 10/1936 | Heath . |
| 2,084,883 | 6/1937 | Atchison . |
| 2,161,293 | 6/1939 | Heath . |
| 2,234,254 | 3/1941 | Hull . |
| 2,640,329 | 6/1953 | Ingvardsen . |
| 2,650,882 | 9/1953 | Sperti ................................ 62/78 X |
| 2,687,622 | 8/1954 | Robbins ............................ 62/458 X |
| 2,690,002 | 9/1954 | Grenell . |
| 2,732,688 | 1/1956 | Dickson . |
| 2,759,339 | 8/1956 | Kundert . |
| 2,992,545 | 7/1961 | Walker ................................. 62/515 |
| 3,308,635 | 3/1967 | Tenniswood et al. ................. 62/277 |
| 3,406,531 | 10/1968 | Swenson et al. ................... 62/78 X |
| 3,777,507 | 12/1973 | Burton et al. .......................... 62/306 |
| 3,782,132 | 1/1974 | Lohoff .................................. 62/260 |
| 3,832,862 | 9/1974 | Ingels .................................. 62/227 |
| 3,922,879 | 12/1975 | Arnold ................................. 62/458 |

Primary Examiner—Lloyd L. King
Attorney, Agent, or Firm—Browdy and Neimark

[57] ABSTRACT

A cold plate for maintaining specimen samples for dissection at desired cooled temperatures includes a metal plate having an aperture therethrough to receive a removable dark frosted glass piece capable of transmitting light therethrough. The metal plate is equipped with an integrally embedded hollow matrix of tubing to circulate a cooling medium delivered from a remotely operated refrigeration system. In addition, a remotely-operated lighting system is provided to illuminate the dark frosted glass piece and the surrounding regions.

10 Claims, 5 Drawing Figures

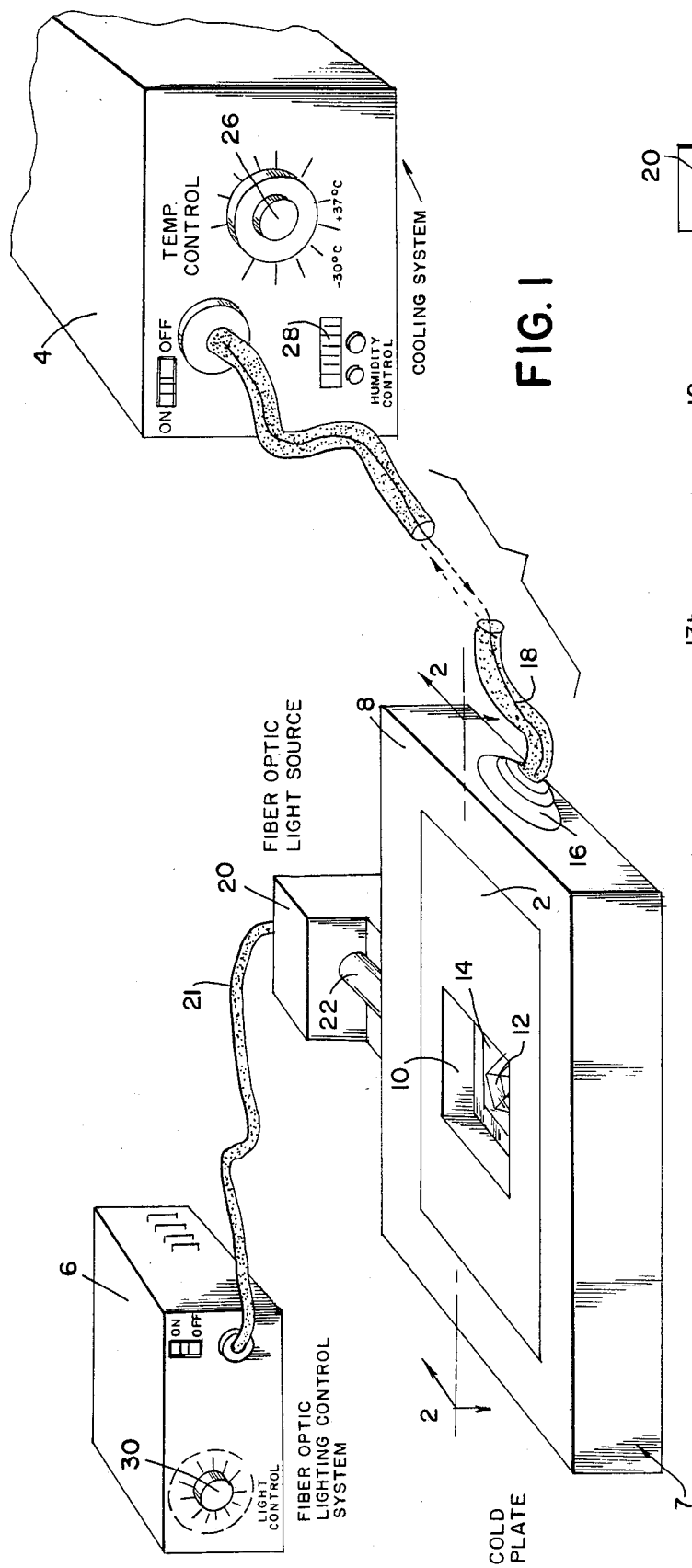
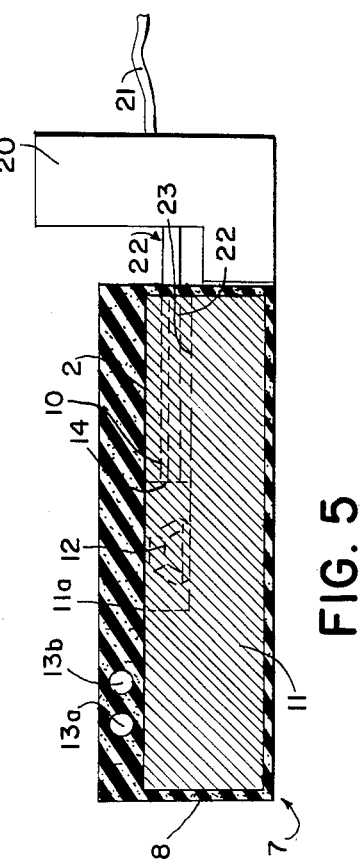

4,615,183

COLD PLATE FOR LABORATORY USE

FIELD OF THE INVENTION

The present invention relates to a cold plate for laboratory use, particularly useful for tissue micro and macro dissection procedures.

BACKGROUND OF THE INVENTION

The usage of cold plates for laboratory dissection has been well known for many years. Previously, cold plates generally included a petry dish or plate supported by a receptacle holding ice or dry ice to maintain a specimen sample at a refrigerated temperature during dissection. However, these particular cold plates can not maintain a sample at a frozen temperature of −20° C. or even at a refrigerated temperature somewhat above 0° C. for long periods of time which are necessary when dissecting some samples, such as brain tissue. In addition, the plates are not uniformly cooled, enabling portions of a sample to thaw prematurely before the completion of a dissection experiment. Furthermore, circularly shaped plates also present the problem of premature sample thawing when a sample is positioned near the periphery of the plate due to the difficulty in cooling the peripheral regions of a circular cold plate.

In more recent years, attempts have been made to mount a plate near or on a refrigerated rod to keep a plate at a frozen temperature. However, these plates only cool the region of the plate in contact with the refrigerated rod or coil preventing uniform cooling. Consequently, these plates are provided only in a very small size, and even so the only spot that maintains constant temperature is directly over the rod, with samples on the periphery tending to thaw.

Refrigerated plates, which are generally used in ice boxes and on counter tops have been used for many years to refrigerate or cool foods. For example, U.S. Pat. Nos. 2,640,329 to Ingvardsen and 2,759,339 to Kundert, both show cold plates including an embedded matrix of hollow tubing to circulate a refrigerant delivered from a remote refrigeration unit to cool the plate to a desired temperature. However, these abovementioned patents only disclose cold plates used for cooling food and are not constructed or capable to be utilzed for dissection procedures.

The U.S. Pat. No. 3,832,862 to Ingels, discloses a laboratory refrigeration apparatus which includes an open well type refrigerator unit for specimens. No provision is made for incorporating a dissection cold plate to the refrigeration unit.

Moreover, no prior laboratory dissection plate is known which includes a light source below the plate's cutting surface to illuminate the sample and the plate during dissection at cooled temperatures. No cold plate used for dissection purposes has previously been available which is capable of uniformly cooling the plate to any desired sub-freezing temperatures and which includes a light source to illuminate the working surface of the plate, nor has there been provided a receptable to support the entire refrigerated plate for preventing direct contact with the cold plate by a scientist or technician when in use.

SUMMARY OF THE INVENTION

Accordingly, it is an object of the present invention to overcome the deficiences of the prior art, such as those set forth above.

It is another object of the present invention to provide for the improved dissection of frozen tissues.

It is a further object of the present invention to provide an improved cold plate for tissue micro and macro dissection, such as the dissection of brain tissue.

It is yet another object of the present invention to provide a dissection cold plate which will cool uniformly.

It is still another object of the present invention to provide a cold plate incorporated with a remotely operated refrigeration unit to cool the plate to any desired cold temperature.

It is another object of the present invention to provide a cold plate equipped with a remotely operated light source to illuminate the plate and a sample on the plate.

It is still another object of the present invention to provide a cold plate with a protective holding receptable.

It is still another object of the present invention to provide a cold plate which will not prematurely thaw a sample placed thereon.

Still other objects, features and attendant advantages of the present invention will become apparent from a reading of the following detailed description of embodiments constructed in accordance therewith, taken in conjunction with the accompanying drawings.

BRIEF DESCRIPTION OF THE DRAWINGS

FIG. 1 is a perspective view of the cold plate of the present invention showing the cold plate in operational use with cooling and illuminating systems;

FIG. 5 is a cross-sectional view of the cold plate taken along line 5—5 in FIG. 3.

DESCRIPTION OF PREFERRED EMBODIMENT

Figure 2:
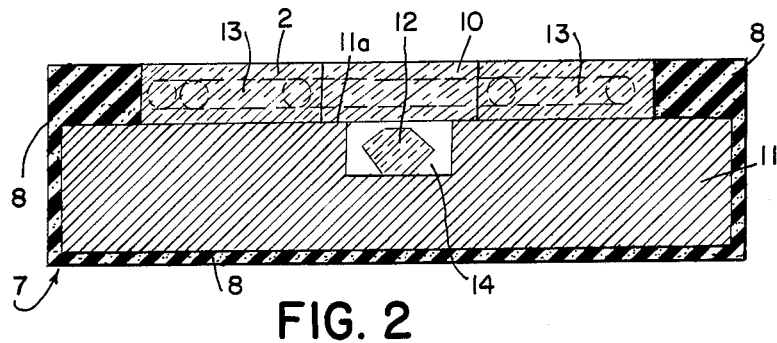
FIG. 2 is a cross-sectional view of the cold plate taken along line 2—2 in FIG. 1.

The presently preferred embodiment is illustrated in FIG. 1 of the drawings, and comprises a cold plate 2, a cooling system 4, a fiber optic lighting control system 6, and a protective holding receptable 7 for supporting and insulating the entire cold plate 2.

The cold plate 2 is preferably of rectangular configuration and is suitably made from a highly heat conductive metal such as aluminum or copper, it being understood that other materials such as stainless steel could also be used; copper is preferred. The cold plate 2 includes a suitably shaped opening near its center region to receive a removably positioned dark frosted glass piece 10. Such piece 10 may also be formed of synthetic glass, e.g. hard plastic, and is preferably of the same thickness of the cold plate which acts as a cutting surface when performing dissection procedures.

Furthermore, the cold plate 2 is provided with an integrally embedded and tightly packed matrix of hollow tubing 13 (see FIGS. 2 and 3) which passes through most of the interior regions of the plate 2 and entirely surrounds dark frosted glass piece 10. The hollow tubing 13 is capable of circulating a refrigerant, such as Freon, or a liquid (such as methanol) which has been cooled down to −40° C. or lower, into the interior of the cold plate 2 delivered from the remotely operated cooling system 4 (such as a FTS refrigeration unit) by means of tubing 18. The cooling system 4 desirably incorporates a temperature control 26 and humidity control 28 so that the user can select the desired temperature of the circulating medium. It should be understood that due to the use of the cooling system, the cold plate 2 can be maintained or cooled to any desired temperature, suitable for dissection purposes, such as to sub-freezing (e.g. −20° to −30° C.) or higher temperatures.

Figure 3:
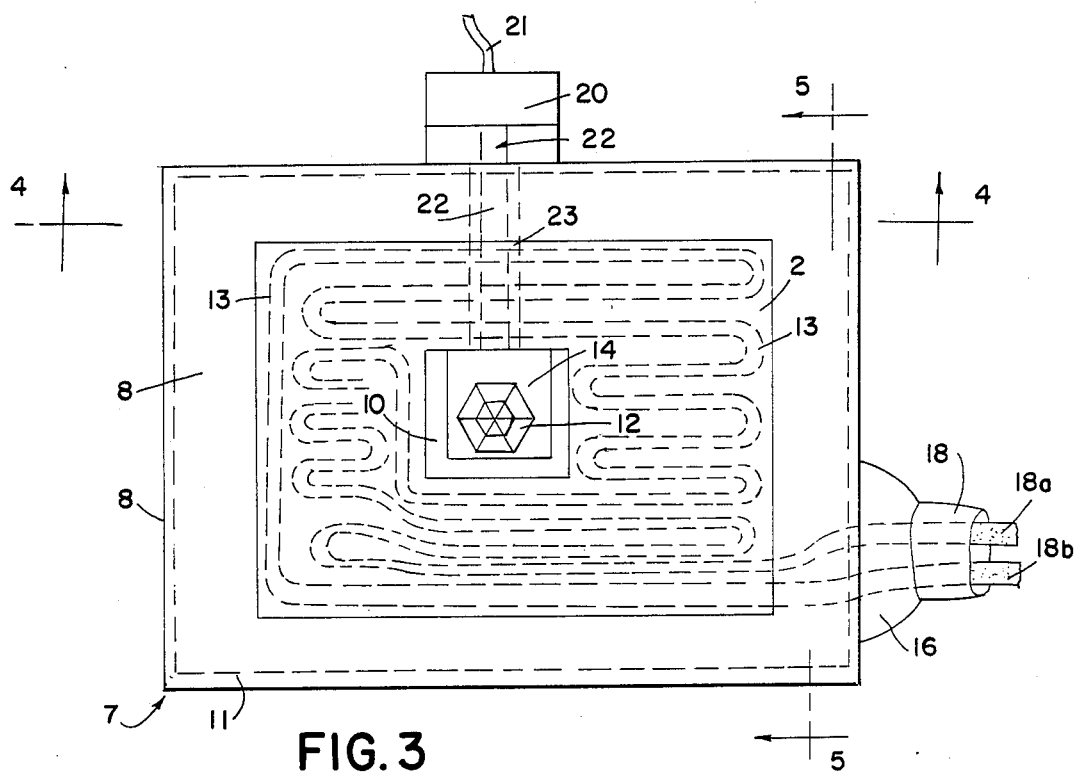
FIG. 3 is a top view of the cold plate of the present invention with a "see through" view of the underlying refrigeration coils.

To prevent direct contact with the cold plate 2 during dissection, a protective holding receptable or tub 7 is provided to hold, support and insulate the plate 2, including a substantially solid rectangularly shaped support 11, which acts as a cold sink and is preferably formal of metal, and which is partially encapsulated in a plastomeric and elastomeric foam 8, such as foam polyurethane or closed cell foam rubber or the like. As best shown in FIGS. 2 and 3, the foam 8 entirely surrounds the perimeter of the plate 2 and metal support 11 to prevent direct contact with the plate 2 when a technician or scientist is leaning over the plate to perform dissection experiments, as well as providing good thermal insulation to prevent adsorption of heat by the cold plate when in use, from the surrounding environment.

The support 11 is equipped with a square shaped cavity 14 to hold a prism 12 beneath the plane of the top surface of the support 11 for placement of the prism 12 just below the dark frosted glass piece 10. In the illustrated embodiment, the supporting surface 11 (see FIG. 2) acts to hold the frosted glass 10 in the same support plane as the cold plate 2. The various elements can be disassembled for periodic cleaning of the glass plate 10 and/or cold plate 2 when necessary. It should be understood that glass piece 10 can be permanently positioned in the cold plate opening, in which case a rigid rubber seal (not shown) should be provided between the glass and the plate to prevent samples from entering into the cavity 14.

Figure 4:
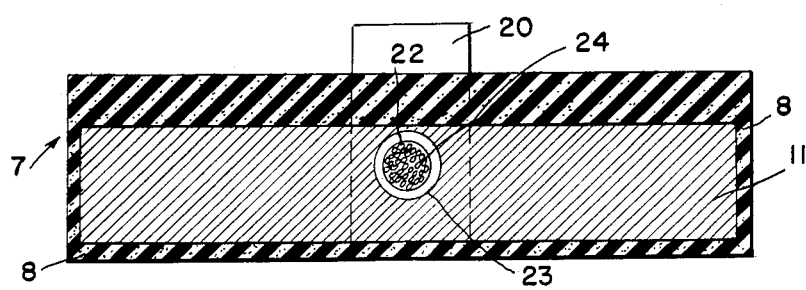
FIG. 4 is a cross-sectional view of the cold plate taken along line 4—4 in FIG. 3.

Referring now to FIGS. 4 and 5, the metal support 11 is provided with a conduit 23 bored into its back side wall just below the support's top surface and extending to the prism holding cavity 14 for receiving fiber optic tubing 22 carrying fiber optic elements 24 from a fiber optic light source. The fiber optic light source 20, shown as being positioned directly behind the cold plate 2, can also be remotely positioned away from the plate 2 if so desired.

An illumination control device 6, which provides light through the dark frosted glass piece 10 to the dissecting surface and surrounding regions, controls the light source 20 by means of electrical cord 21 (see FIG. 1), and is itself controlled by the operator using a remotely operated light control dimming means 30. The illumination system provides remotely controlled light from the light source 20 to the cold plate by projecting light to the prism 12 in the cavity 14 via fiber optic elements 24, the prism 12 redirecting the light upwardly and thereby illuminating the dissecting surface 10 and the surrounding regions. It should be understood that any type of semi-transparent device may be utilized in place of the dark frosted glass, as long as the device can transmit light therethrough. Also the glass 10 should be dark frosted to prevent glare and provide contrast when light is transmitted therethrough. If desired, a second light, preferably a second fiber optic, shines over the entire upper surface to provide top lighting.

When assembling the cooling system 4 to the cold plate by means of tubing 18, a hook-up plug 16 is provided at one end of the tubing 18 to mate tubes 18a and 18b with inlet and outlet ports 13a and 13b of the hollow matrix tubing 13 (see FIGS. 2 and 5). Note, that the hook-up plug 16 is assembled to the cold plate through a passage provided in the rubberized foam 8 of the protective holding receptable 7 (not shown).

It should be understood that tub 7 may be formed of solid plastic such as acrylic plastic (e.g. Plexiglas) or the like, and the support 11 may be made from other materials, such as rubber or plastic, to keep the cold plate system lightweight and easy to move.

It should be further understood that any type of refrigeration system or lighting system may be employed so long as the refrigeration system can cool and maintain that plate at any desired temperature, and as long as the lighting system can direct light to the underside of the dissecting surface. Also, cold plate 2 could be of any shape or size so long as the entire surface can be uniforming cooled.

When in operational use, a scientist or technician can place a tissue sample on the working surface 10 to be dissected. If a particular sample is not needed at that moment for dissection, that sample can be moved to the surface of the plate 2 to keep the sample at a desired temperature until it is necessary for closer examination, at which time the sample could be moved back to working surface 10. Moreover, the user can remotely control the desired temperature of the cold plate and the amount of light to pass through the dissecting surface.

It will be obvious to those skilled in the art that various other changes and modifications may be made without departing from the scope of the invention and the invention is not to be considered limited to what is shown in the drawings and described in the specifications.

What is claimed:

1. A dissection cold plate for maintaining laboratory specimens at desired cooled temperatures, and dissecting said specimens thereon, comprising:

a metal cooling plate having a generally planar upper surface with an aperture therethrough, said plate including an integrally embedded hollow matrix of tubing therein, said tubing adapted to generally surround said aperture;

semi-transparent or translucent means removably positioned in said aperture, said semi-transparent means having a generally planar upper surface lying in the plane of the upper surface of said cooling plate;

remotely-operated cooling means for circulating a cooling medium through said tubing for cooling said metal plate to a desired temperature;

remotely-operated lighting means for illuminating said semi-transparent means from below its upper surface; and protective covering and insulating covering means for surrounding and insulating said metal plate.

2. A dissection cold plate according to claim 1 further comprising supporting means for supporting and insulating said metal plate and said semi-transparent means, said supporting means including, as part of said lighting means, means for transmitting light therethrough to the underside of said semi-transparent means.

3. A dissection cold plate for maintaining laboratory specimens at desired cooled temperatures, and dissecting said specimens thereon, comprising:

a metal cooling plate having a generally planar upper surface with an aperture therethrough, said plate including an integrally embedded hollow matrix of tubing therein, said tubing adapted to generally surround said aperture;

semi-transparent or translucent means removably positioned said aperture, said semi-transparent means having a generally planar upper surface lying in the plane of the upper surface of said cooling plate;

remotely-operated cooling means for circulating a cooling medium through said tubing for cooling said metal plate to a desired temperature;

remotely-operated lighting means for illuminating said semi-transparent means from below its upper surface means, wherein said remotely-operated lighting means comprises a prism and fiber optic bundle, said prism being positioned directly underneath said semi-transparent means, whereby light from an illumination source is directed by means of said fiber bundle to said prism redirecting the light to said semi-transparent means; and protective covering and insulating covering means for surrounding and insulating said metal plate.

4. A cold plate in accordance with claim 2, wherein said supporting means further includes a recessed region for supporting a prism, and a conduit region for supporting a fiber optic bundle.

5. A cold plate in accordance with claim 1, wherein said semi-transparent means comprises a dark frosted glass piece.

6. A cold plate in accordance with claim 1, wherein said remotely-operated cooling means further comprises a hook-up means for mating said cooling means to said tubing in said metal plate.

7. A cold plate in accordance with claim 2, wherein said supporting means is adapted to support said metal plate and said semi-transparent means in substantially the same plane.

8. A cold plate in accordance with claim 1, wherein said protective covering means is made of insulating foam material.

9. A cold plate in accordance with claim 1, wherein said cooling means and said lighting means include control means.

10. A dissection cold plate for maintaining laboratory specimens at desired cooled temperatures and for dissecting the cooled specimens thereon, comprising:

a cooling plate formed of material having good heat conductivity and having a generally planar upper surface with a cavity therein, said plate including cooling means surrounding said cavity;

semi-transparent or translucent means removably positioned over said cavity, said semi-transparent means having a generally planar upper surface lying in the plane of the upper surface of said cooling plate;

means for activating said cooling means for cooling said cooling plate to a desired temperature;

lighting means for illuminating said semi-transparent means from below its upper surface, said lighting means including a prism and means to direct light to said prism, said prism being positioned directly underneath said semi-transparent means, whereby light entering said prism is redirected to said semi-transparent means; and protective and insulating covering means for surrounding and insulating said cooling plate.

* * * * *

UNITED STATES PATENT AND TRADEMARK OFFICE
CERTIFICATE OF CORRECTION

PATENT NO. : 4,615,183

DATED : October 7, 1986

INVENTOR(S) : Juncos et al

It is certified that error appears in the above-identified patent and that said Letters Patent is hereby corrected as shown below:

[75] Inventors: change "Silver Springs" to --Silver Spring--

Column 3, line 21: change "formal" to --formed--;

Signed and Sealed this

Third Day of February, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,615,183

DATED : October 7, 1986

INVENTOR(S) : Jorge L. Juncos et al.

It is certified that error appears in the above-identified patent and that said Letters Patent is hereby corrected as shown below:

Column 6, line 22, insert --of dark frosted material-- after "means".

Signed and Sealed this

Seventh Day of April, 1987

Attest:

DONALD J. QUIGG

Attesting Officer

Commissioner of Patents and Trademarks